United States Patent [19]

Ueno

[11] Patent Number: 5,080,890

[45] Date of Patent: Jan. 14, 1992

[54] PERMANENT WAVING LOTION AND A PROCESS FOR PERMANENT WAVING OF HAIR

[75] Inventor: Yuzo Ueno, Yokohama, Japan

[73] Assignee: Loumar Cosmetics K.K., Tokyo, Japan

[21] Appl. No.: 610,965

[22] Filed: Nov. 9, 1990

[30] Foreign Application Priority Data

Nov. 16, 1989 [JP] Japan .................................. 1-298695

[51] Int. Cl.$^5$ .......................... A61K 7/11; A61K 7/09; A45D 7/06; A45D 7/04
[52] U.S. Cl. ........................................ 424/71; 424/72; 132/204; 132/206; 132/209
[58] Field of Search ............................. 424/71, 72, 62; 514/769, 771; 132/204, 206, 209

[56] References Cited

U.S. PATENT DOCUMENTS 4,349,537  9/1982  Forbriger, Jr. ........................ 424/71
4,426,376  1/1984  Shirakura et al. ..................... 424/71
4,770,872  9/1988  Hsiung et al. ......................... 424/71

Primary Examiner—Thurman K. Page
Assistant Examiner—Susan S. Rucker
Attorney, Agent, or Firm—Wenderoth, Lind & Ponack

[57] ABSTRACT

The second lotion used for permanent wave process by two lotions method comprising a hydrogen peroxide solution having a pH value in excess of 4.5, but not exceeding 7.5 and a hydrogen peroxide concentration of 0.3 wt % or lower, and a process for permanent waving of hair using the said hydrogen peroxide solution as the second lotion.

In the process for permanent waving of hair according to the invention, treating with the second lotions preferably carried out at a temperature of 37°~40° C.

Use of the permanent waving lotion of the present invention can prevent damage of the hair due to the decline of modulus of the hair after repeated permanent waving process.

3 Claims, 5 Drawing Sheets

PERMANENT WAVING LOTION AND A PROCESS FOR PERMANENT WAVING OF HAIR

BACKGROUND OF THE INVENTION (1) Field of the Invention

The present invention relates to a permanent waving lotion and a process for permanent waving of hair. More particularly, the present invention relates to the second lotion for permanent waving of hair comprising a hydrogen peroxide solution having certain properties such that consecutive decline of the modulus of the hair due to repeated permanent waving processes can be prevented, and a process for permanent waving of hair using said second lotion.

(2) Description of the Prior Art

As the means to impart a lasting curl to hair, which is so-called "cold waving" the means of achieving permanent waving without any need for heat using an aqueous alkaline solution, is conventionally adopted instead of the method which depends on heating of the hair to a high temperature.

The cold waving method is usually performed in the manner as described in the following:

First of all, strands of hair is wound around rods, a reducing agent consisting of a mixture of ammonium thioglycolate, ammonium bicarbonate, ammonia water and the like is applied to the strands of hair as the first lotion, and the head wrapped up in a cap is allowed to stand for about 5 to 20 minutes. By aforesaid treatments, cleavage of the disulfide bond (—S—S—) in keratin fiber of the hair is ruptured, and the hair is consequently plasticized and a deformation of the strands of hair is given. And then the reducing process is terminated by either once removing the first lotion (the reducing agent) or neutralizing the reducing agent by an acidic solution. At this stage many disulfide groups in keratin fiber of the hair have changed into mercapto groups (—SH). Next, the deformation given to the strands of hair is fixed by means of applying to them sodium bromate solution or hydrogen peroxide solution as the second lotion (the oxidizing agent) and then allowing them to stand for about 15 minutes to have the SH groups to be oxidized and converted back into disulfide groups. Finally, the second lotion is rinsed off and the hair is dried to complete the cold waving.

People who have their hair permed visit beauty shops ordinarily every two or three months in their efforts to continually impart a curl to their hairs.

However, according to the conventional process, it has been inevitable for the processed hair to become law stiffness, coarse and lusterless, so-called "damaged hair", inasmuch as modulus of the hair is reduced and its surface smoothness and gloss decreases due to the reducing step and oxidizing step which is inevitably undergoes repeatedly.

In the past, there have been proposed methods to overcome development of damages to the hair. Such methods include use of cysteine or the like as a weaker reducing agent which is obtained by modifying the composition of the conventional first lotion, changing of the pH value or concentration of the first lotion, and admixing of additives to the first lotion or second lotion. Neither one of the said methods, however, has proved effective to prevent consecutive decline in the modulus of the hair by repeated permanent wavings.

SUMMARY OF THE INVENTION

It is the object of the present invention to provide an oxidizing agent which is suitably used as the second lotion in the permanent waving.

The present inventor assumed that the principal cause of the decline in modulus of the hair lies in the oxidizing step for which the second lotion is used, rather than the reducing step for which the first lotion i used. Furthermore, the present inventor noticed that in case where hydrogen peroxide is used as the second lotion, properties of the hydrogen peroxide solution influences the rate of decline in the modulus to a large extent, while the chemicals which are in predominant use today are sodium bromate and hydrogen peroxide.

The present inventor has found, through researches, that the decline in modulus of elasticity can be prevented by using hydrogen peroxide having certain properties, and the inventor has also found the preferable condition for permanent waving of hair using such hydrogen peroxide as the second lotion.

The present invention is a permanent waving lotion consisting of a hydrogen peroxide solution having a pH value in excess of 4.5, but not exceeding 7.5, and a hydrogen peroxide concentration of 0.3 wt. % or lower, and a process for permanent waving of hair which comprises treating hair with the keratin-reducible first lotion for permanent waving before and/or after mechanical shaping of hair, rinsing the hair, and oxidizing and fixing the shaped hair by treating the hair with the said permanent waving lotion as the second lotion.

DETAILED DESCRIPTION OF THE PREFERRED EMBODIMENTS

Figure 1:
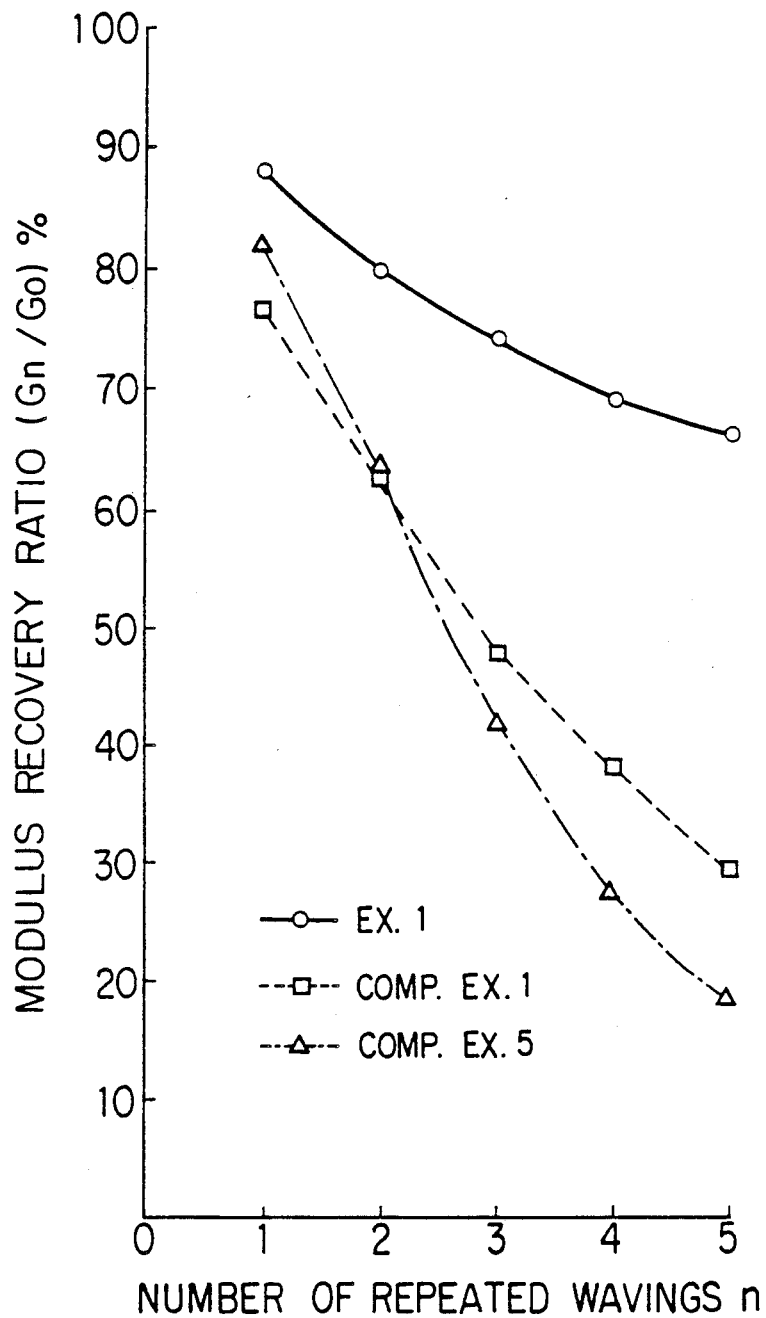
FIG. 1: Depicts changes in the Modulus Recovery Ratio due to repeated permanent wavings and is described in more detail in Example 1.

Hydrogen peroxide, as well as sodium bromate, is most commonly used as the second lotion for the permanent waving. The hydrogen peroxide solution which is conventionally used as the second lotion has a pH value falling within the range of 2.5 to 4.5 and 1.5 to 2.5 wt. %.

The second lotion in the present invention is higher in alkalinity than that of the hydrogen peroxide solution adopted as the second lotion for the conventional permanent waving lotions. More specifically, the second lotion in the present invention has a pH value in excess of 4.5, but not exceeding 7.5, and preferably in the range of 4.7 to 7.0, or more preferably in the range from 5.0 to 6.5. Lotions having a pH value of 4.5 or lower causes declines in the modulus of the hair after repeated permanent waving processes. On the other hand, the lotions having a pH value higher than 7.5 has a drawback that the hair tends to readily suffer damages, and, moreover, the modulus decreases.

The hydrogen peroxide solution as the second lotion in the permanent waving process is prepared by adding to the commercial hydrogen peroxide a buffer solution based on phosphoric acid or citric acid.

In the present invention, the pH value of the buffer solution can be adjusted to fall within the range of 4.5 to 7.5 by changing the recipe of the buffer solution.

The hydrogen peroxide concentration in the present invention is 0.3 wt. % or lower, and preferably not lower than 0.01 wt. %. In cases where the hydrogen peroxide concentration is higher than 0.3 wt. %, the ratio of recovery of modulus (Modulus Recovery Ratio) declines. On the other hand, in cases where the concentration is lower than 0.01 wt. %, it takes a longer time for treatment and the oxidation is apt to be incomplete. The "hydrogen peroxide concentration" as herein used means the H2O2 content (wt. %) of a solution obtained by diluting the commercial hydrogen peroxide solution which normally has a H2O2 concentration of 30 wt. %.

The present invention also includes a process for permanent waving of hair using said lotion as the second lotion for permanent waving. In the invention of a process for permanent waving, strands of hair are mechanically shaped by winding around suitable body such as rods, before and/or after mechanical shaping, hair is treated with the keratin-reducible first lotion for permanent waving. After contacting of hair with the first lotion for a given time, hair is rinsed. After that the hair is treated with the second lotion according to the present invention for a given time. By these treatments hair is oxidized and curl in the hair is fixed and permanent waving process is achieved.

As mentioned above, according to the present invention, although decline in he modulus can be improved remarkably, oxidation reaction remains incomplete in some part of hairs depending on a treating condition due to the use of low concentration hydrogen peroxide. Consequently, sometimes phenomena of so-called "wave-down" which means loosing of shaped wave will be observed.

However the present inventor has found that disadvantage of such wave down can be overcome by carrying out the treating with the second lotion at the temperature of 37°~47° C., preferably 40°~45° C.

So it is preferable that treatment of the hair with the second lotion is carried out at a temperature between between 37° and 47° C., preferably 40° and 45° C. for 2 to 15 minutes in the present invention.

In the present invention, any first lotions may be selected from the ones which are commonly used. There may be cited thioglycolic acid, ammonium thioglycolate and cysteine as examples of such first lotion.

It is preferable that a buffer solution is added to the second lotion in the present invention to prevent abrupt changes in the pH value, since the pH value of the second lotion in some instances suffer changes to the extent that the effects of the present invention are impaired as a result of contact made between the second lotion and the hair when the lotion is applied to the hair.

Variety of additives may be added to the second lotion for permanent waving in the present invention, consisting of an aqueous solution of hydrogen peroxide for the purpose of enhancing the activity of the permanent waving lotions to such extent as will not hamper the object and effects of the present invention. There are cited as examples of such additives products of hydrolysis of protein or the like. Besides, such additives as, for example, mink oil, silicone and the like may be compounded for the purpose of improving the touch feeling of the hair which is felt after the permanent waving process.

EXAMPLES

The present invention will now be described in detail with reference to the following examples that by no means limit the scope of the invention.

EXAMPLE 1

From among natural hairs collected from a healthy adult female who has not undergone any permanent waving, nor any hair dyeing, in her life, unfrizzed normal hairs having diameters falling in the range of 55 to 60 microns were selected as test specimens.

A glass column provided with a temperature regulating device was mounted on a tensile testing instrument, and a hair of 12.0 cm length was positioned inside the column and was fastened at its both ends by chucks. The hair in the column filled with distilled water was allowed to stand for 15 minutes. The hair as subjected to a stress to the extent that the tensile strain (deformation) thereby produced has reached 1.5%, and the stress at this point was measured and recorded as the "initial modulus (G0) before the permanent waving process."

Next, water was discharged from the column, which was then replaced with the first lotion for permanent waving consisting of ammonium thioglycolate, ammonium bicarbonate and ammonia water, having the ammonium thioglycolate concentration of 6% and the pH value of 9.0.

As the reducing process proceeded, the stress gradually relaxed.

Such stress relaxation curve was recorded on the chart paper, and at such point where the stress reaches to 30% against the initial stress at 1.5% strain, the first lotion in the column was removed and the interior of the column was rinsed with distilled water.

The column was filled with the second lotion consisting of an aqueous solution of hydrogen peroxide having the pH value of 5.6 and the concentration of 0.03 wt. % and the charged column was kept at 30° C. and allowed to stand for 15 minutes and, then, the second lotion was removed from the column and the interior of the column was rinsed with distilled water. After the hair was allowed to stand for 15 minutes, the modulus of the hair was measured again. The Modulus Recovery Ratio ($G_n/G_0$) was calculated by dividing [the modulus of elasticity recorded after the n times repeated permanent waving process ($G_n$)] by [the modulus recorded on the chart paper at a constant strain (1.5%) given in water to the hair prior to addition of the first lotion (G0)].

The said permanent waving process was repeated five times and the modulus ($G_1 \sim G_5$) was measured after each permanent waving for the five times consecutive permanent wavings. And the Modulus Recovery Ratio after each permanent waving was calculated, namely, G1/G0, G2/G0, G3/G0, G4/G0, and G5/G0.

The results of those measurements are shown in Table 1.

Changes which occurred in Modulus Recovery Ratio due to the repeated permanent wavings are shown in FIG. 1.

EXAMPLES 2, 3, 4, 5 and 6
COMPARATIVE EXAMPLES 1, 2, 3, and 4

Using the hydrogen peroxide solutions of the pH values and concentrations as set forth in Table 1 as the second lotion, three to five times repeated permanent waving tests were carried out in accordance with the same procedures as those followed in Example 1 on normal hairs collected from the same donor as in the case of Example 1 at spots near the spot where the hairs used in Example 1 were collected. Results of these tests are also shown in Table 1.

As regards the results of Comparative Example 1, changes in Modulus Recovery Ratio in consequence of repeated permanent wavings are set forth in FIG. 1.

Figure 2:
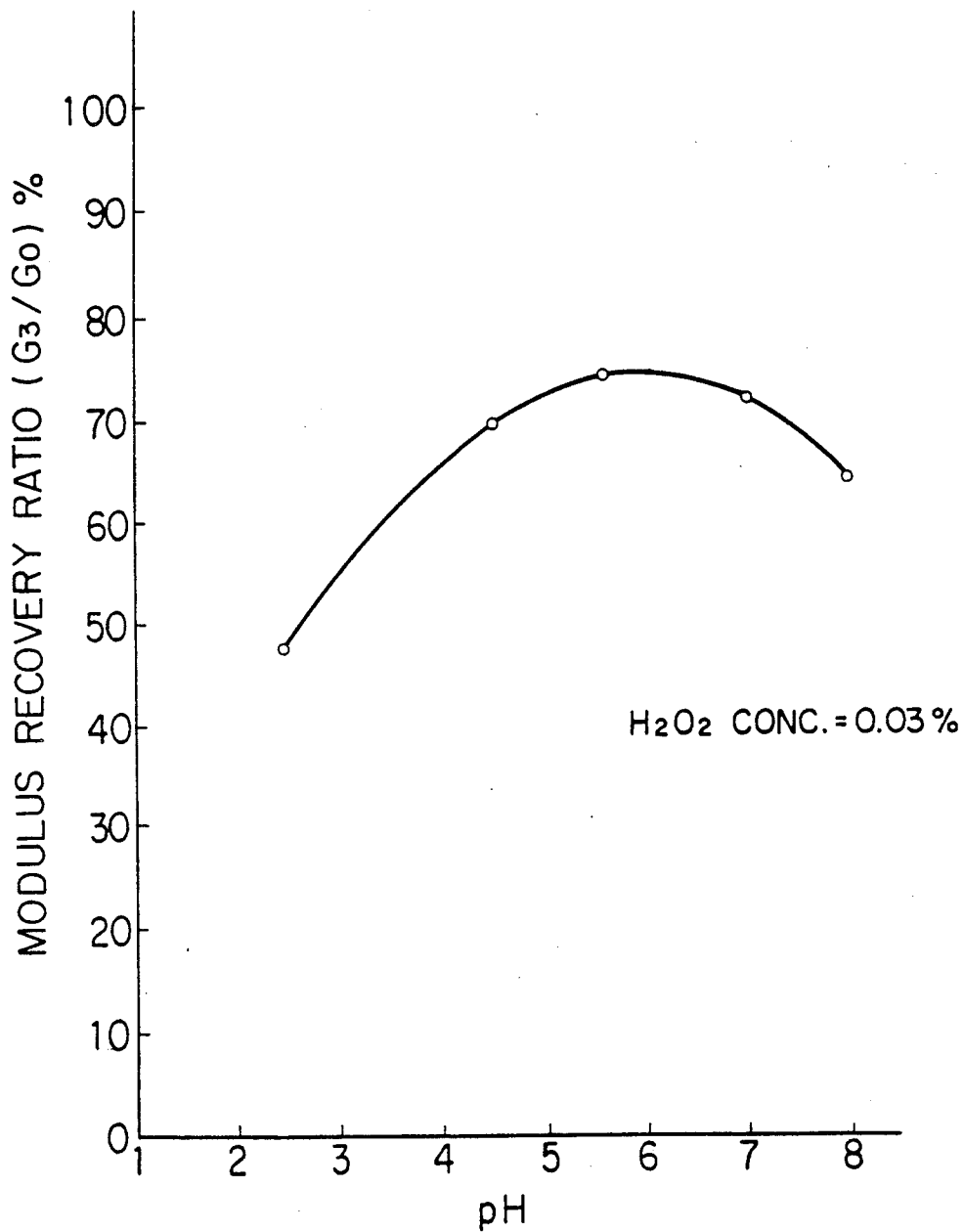
FIG. 2: Depicts the relationship between the Modulus Recovery Ratio and pH for a specified concentration of hydrogen peroxide. See Examples 2-6 and Comparative Examples 1-4 for a detailed description.

The relationship between Modulus Recovery Ratio after three times repeated permanent wavings ($G_3/G_0$) and the pH value of aqueous solution of hydrogen peroxide is shown in FIG. 2 on the basis of the results of Examples 1, 2 and 3 and Comparative Examples 1 and 2.

Figure 3:
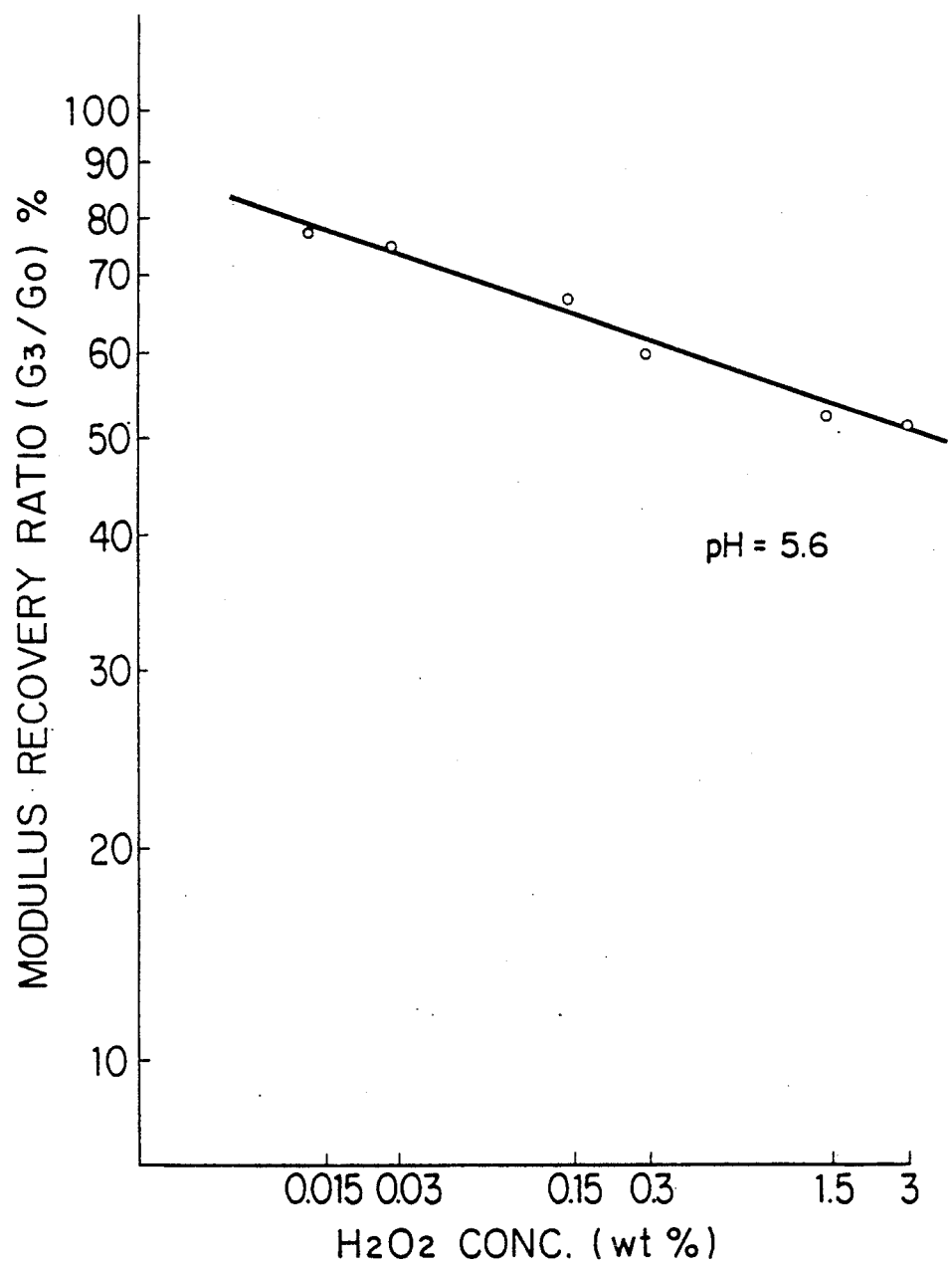
FIG. 3: Depicts the relationship between the Modulus Recover Ratio and concentration of hydrogen peroxide for a specified pH. See Examples 2-6 and Comparative Examples 1-4 for a detailed description.

Furthermore, the relationship between Modulus Recovery Ratio after three times repeated permanent wavings ($G_3/G_0$) and the concentration of aqueous solution of hydrogen peroxide is shown in FIG. 3 on the bases of the results of Examples 1, 4, 5, and 6 and Comparative Examples 3 and 4.

TABLE 1

| | Properties of aq. solution of Hydrogen peroxide | | Modulus Recovery Ratio after the Permanent Waving $G_n/G_0$ (%) | |
|---|---|---|---|---|
| | pH | Concentration (Wt %) | | |
| Example 1 | 5.6 | 0.03 | $G_1/G_0$ | 87.7 |
| | | | $G_2/G_0$ | 79.8 |
| | | | $G_3/G_0$ | 74.2 |
| | | | $G_4/G_0$ | 69.2 |
| | | | $G_5/G_0$ | 62.7 |
| Example 2 | 4.6 | 0.03 | $G_1/G_0$ | 83.4 |
| | | | $G_2/G_0$ | 76.9 |
| | | | $G_3/G_0$ | 69.8 |
| | | | $G_4/G_0$ | 64.1 |
| Example 3 | 7.0 | 0.03 | $G_1/G_0$ | 86.5 |
| | | | $G_2/G_0$ | 79.6 |
| | | | $G_3/G_0$ | 72.4 |
| Example 4 | 5.6 | 0.015 | $G_1/G_0$ | 88.6 |
| | | | $G_2/G_0$ | 82.5 |
| | | | $G_3/G_0$ | 76.2 |
| | | | $G_4/G_0$ | 70.1 |
| Example 5 | 5.6 | 0.15 | $G_3/G_0$ | 67.4 |
| Example 6 | 5.6 | 0.03 | $G_1/G_0$ | 83.8 |
| | | | $G_2/G_0$ | 70.1 |
| | | | $G_3/G_0$ | 57.4 |
| | | | $G_4/G_0$ | 44.7 |
| Comparative Example 1 | 2.5 | 0.03 | $G_1/G_0$ | 76.8 |
| | | | $G_2/G_0$ | 62.6 |
| | | | $G_3/G_0$ | 47.9 |
| | | | $G_4/G_0$ | 38.0 |
| | | | $G_5/G_0$ | 29.6 |
| Comparative Example 2 | 8.0 | 0.03 | $G_1/G_0$ | 85.1 |
| | | | $G_2/G_0$ | 76.2 |
| | | | $G_3/G_0$ | 64.5 |
| Comparative Example 3 | 5.6 | 1.5 | $G_1/G_0$ | 81.5 |
| | | | $G_2/G_0$ | 66.6 |
| | | | $G_3/G_0$ | 50.9 |
| Comparative Example 4 | 5.6 | 3.0 | $G_3/G_0$ | 67.4 |

Comparative Example 5

Using an aqueous solution of sodium bromate (the concentration being 10 wt. %) as the second lotion, permanent waving tests were carried out in accordance with the same procedures as those followed in Example 1 on normal hairs collected from the same donor as in the case of Example 1 at spots near the spot where the hairs used in Example 1 were collected. Results of these tests are shown in Table 2.

The changes in Modulus Recovery Ratio resulting from the repeated permanent wavings are also shown in FIG. 1.

TABLE 2

| | Kind of the second lotion | Modulus Recovery Ratio after permanent wavings ($G_n/G_0$) (%) | |
|---|---|---|---|
| Compartive Example 5 | Sodium bromate | $G_1/G_0$ | 81.9 |
| | | $G_2/G_0$ | 63.1 |
| | | $G_3/G_0$ | 41.8 |
| | | $G_4/G_0$ | 27.4 |
| | | $G_5/G_0$ | 18.2 |

From the results of the above-mentioned Examples and Comparative Examples it is obvious that the decline in the modulus after five times repeated permanent waving processes applying the second lotion in the present invention is equivalent to the level which occurs after twice repeated permanent waving processes depending on the conventional lotion. It is also obvious that the second lotion of the present invention imparts an excellent effect to reduce the decline in modulus of the hair, compared with the conventionally adopted hydrogen peroxide as well as sodium bromate.

Examples 7–11 and Comparative Examples 6–10

Using hydrogen peroxide solutions having the concentrations and the pH values shown in the Table 3, permanent wavings were carried out three times in the same procedure that was followed in Example 1 except that the processing temperature is 45° C., and measurements of Modulus Recovery Ratios ($G_3/G_0$) and Wave Downs at 2 hours after the waving were taken. Results of the tests are set forth in Table 4.

Figure 4:
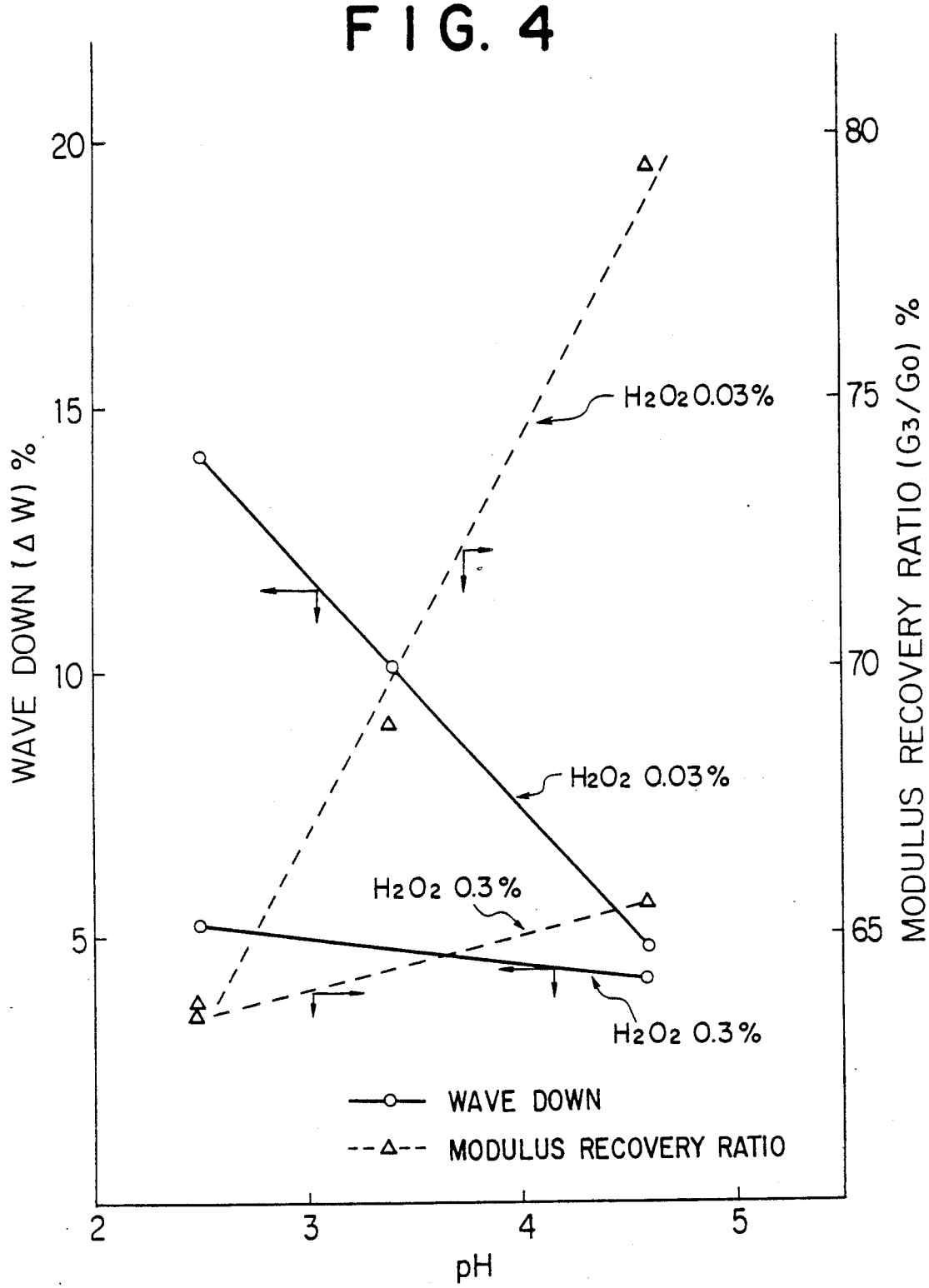
FIG. 4: Depicts the relationship between the pH of the oxidizing solution, the Modulus Recovery Ratio and Wave Down. See Examples 7-11 and Comparative Examples 6-10 for a detailed description.

Indicated in FIG. 4 is the relationship between Modulus Recovery Ratio ($G_3/G_0$) and Wave Down of the hair which has undergone three consecutive permanent wavings at 45° C. and the properties of the hydrogen peroxide solution, data for which being based on the results of above-mentioned Examples and Comparative Examples.

Wave Down of the hair was determined in the following manner.

The Method of Determining Wave Down

After permanent waving was carried out wherein the first lotion and the second lotion were applied in accordance with the procedure described in Example 1, the second lotion was discharged from the column, and the column after a thorough rinse was filled with water.

The movable crosshead of the tensile machine was lifted so as to restore the zero strain level. The column was then allowed to stand for 5 minutes. After switching the chart paper feed speed to the high position and marking a starting point on the chart paper, the crosshead was lowered until the 1.5% strain level was reached.

Since the hair has been elongated by the prior permanent waving, stress occurs at a point before the 1.5% strain level is reached. Since the distance traveled by the crosshead of the tensile machine up to the point where stress emerges depends on the efficiency of permanent waving exerted to the hair, the distance from the starting point to the point where stress occurs is monitored from the chart paper. The efficiency of permanent waving immediately after the permanent waving, $W_0$, is given by the following equation:

$$W_0 = l_0/L \times 100\%$$

ps wherein $l_0$ is the distance traveled by the crosshead to the point where tensile stress occurs, L is the distance traveled by the crosshead up to the point where the strain is 1.5%.

After $W_0$ was measured in the above-mentioned procedure, the tensile machine was so adjusted that the tensile strain level returns to zero, and the specimen was left to stand for any preferred period of time (t minutes). The above-mentioned procedure was repeated. The distance traveled by the crosshead to the point where tensile stress occurs after the lapse of the given time thus measured represents the efficiency of permanent waving. Namely, the efficiency of permanent waving ($W_t$) is given by the following equation:

$$W_t = l_t/L \times 100\%$$

wherein $l_t$ is the distance traveled by the crosshead of the tensile machine to the point where tensile stress occurs after the hair has been left to stand for t minutes, L is the distance traveled by the crosshead to the point where the strain is 1.5%. Wave Down ($\Delta W$) is given as the time-dependent change in the efficiency of permanent waving immediately after completion of the permanent waving by the following equation:

$$\Delta W = (W_t - W_0)/W_0 \times 100\%$$
$$\text{or}$$
$$= (l_t - l_0)/l_0 \times 100\%$$

Example 12

Using hydrogen peroxide solutions having the pH value of 4.6, and the concentration of 0.03 and 0.3 weight %, respectively, as the second lotion and at processing temperatures of 30° C., 35° C., 40° C. and b 45° C., respectively, permanent wavings were carried out three times in the same procedure that was followed in Example 1 and measurements of Modulus Recovery Ratios (G3/G0) were taken.

Furthermore, Wave Down of the hair which has undergone permanent waving was measured. Results of the tests are set forth in Table 4.

Figure 5:
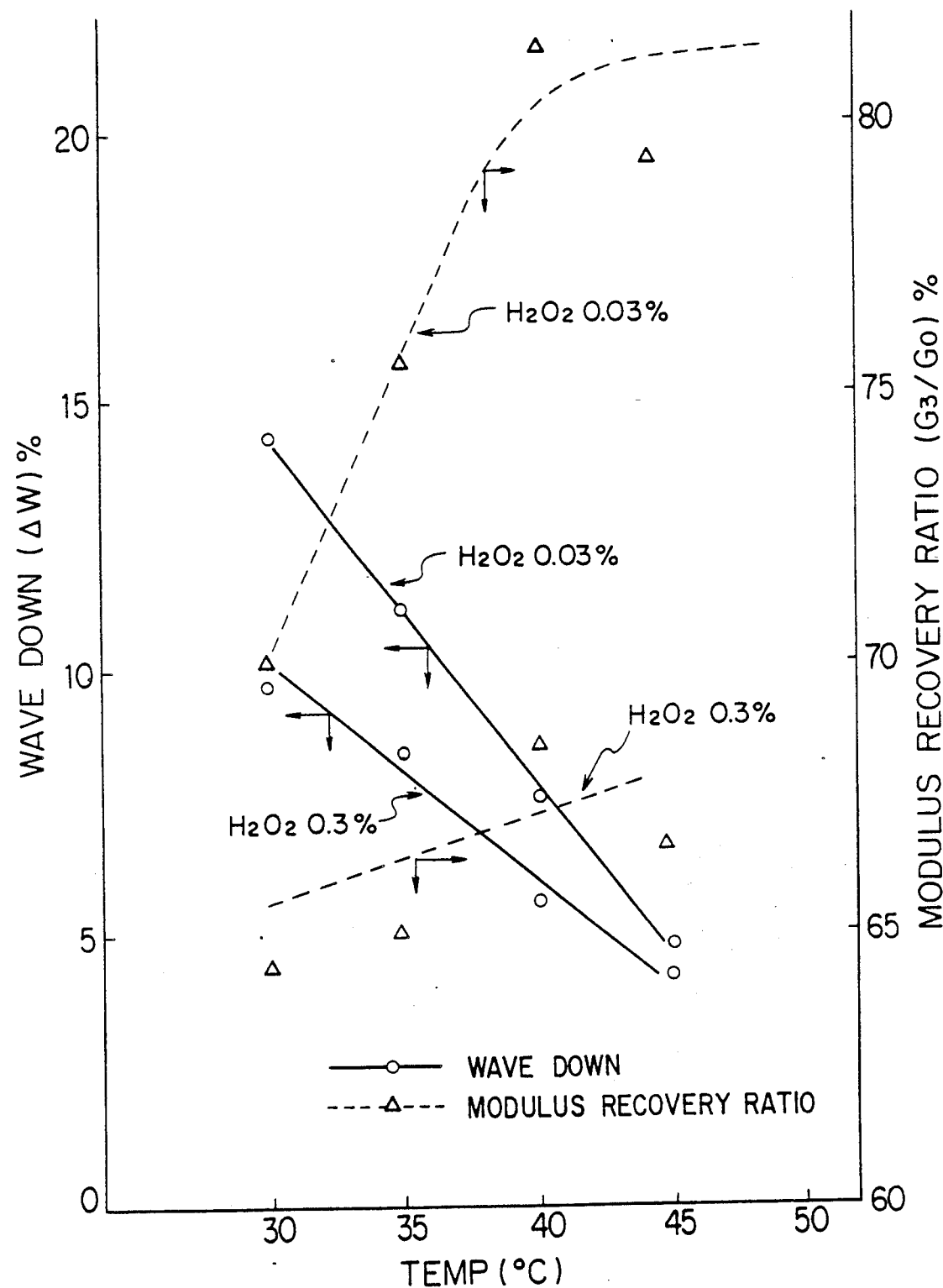
FIG. 5: Depicts the relationship between the temperature of the oxidizing treatment, Wave Down and Modulus Recovery Ratio. See Example 12 for a detailed description.

Indicated in FIG. 5 is the relationship between Modulus Recovery Ratio (G3/G0) and Wave Down of the hair which has undergone three consecutive permanent wavings and the processing temperature of the second lotion, data for which being based on the results of Example 12.

TABLE 3

| Concentration of the Hydrogen peroxide solution (wt. %) | | Modulus Recovery Ratio after the Permanent Waving $G_n/G_0$ and Wave Down (%) (Processing temperature: 45° C.) | | | |
|---|---|---|---|---|---|
| | | pH | | | |
| | | 2.5 | 3.4 | 4.6 | 7.0 |
| | | Comparative Example 6 | Comparative Example 7 | Example 7 | Example 8 |
| 0.03 | $G_1/G_0$ | 79.3 | 88.1 | 89.9 | 88.7 |
| | $G_2/G_0$ | 69.4 | 78.5 | 84.7 | 82.3 |
| | $G_3/G_0$ | 63.5 | 72.7 | 79.4 | 76.9 |
| | WD | 14.0 | 10.0 | 4.8 | 4.3 |
| | | Comparative Example 8 | | Example 9 | Example 10 |
| 0.15 | $G_1/G_0$ | 82.6 | | 86.7 | 84.0 |
| | $G_2/G_0$ | 73.0 | | 77.0 | 73.4 |
| | $G_3/G_0$ | 67.3 | | 70.3 | 67.5 |
| | WD | 5.5 | | 4.8 | 4.2 |
| | | Comparative Example 9 | | Example 11 | |
| 0.3 | $G_1/G_0$ | 81.5 | | 85.5 | |
| | $G_2/G_0$ | 71.1 | | 76.5 | |
| | $G_3/G_0$ | 63.7 | | 66.6 | |
| | WD | 5.2 | | 4.1 | |
| | | | | Comparative Example 10 | |
| 1.0 | $G_1/G_0$ | | | 83.8 | |
| | $G_2/G_0$ | | | 72.0 | |
| | $G_3/G_0$ | | | 57.9 | |
| | WD | | | 4.3 | |

TABLE 4

| | | Modulus Recovery Ratio after the Permanent Waving $G_n/G_0$ (%) and Wave Down (%) (pH: 4.6) | | | |
|---|---|---|---|---|---|
| | | Temperature | | | |
| | | 30° C. | 35° C. | 40° C. | 45° C. |
| Concentration of the Hydrogen peroxide (wt %) | 0.03 $G_3/G_0$ % | 70.0 | 75.5 | 81.4 | 79.4 |
| | WD % | 14.2 | 11.0 | 7.5 | 4.8 |
| | 0.3 $G_3/G_0$ % | 64.3 | 65.2 | 68.5 | 66.6 |
| | WD % | 9.6 | 8.4 | 5.5 | 4.1 |

As is obvious from the results of Examples 7–12 and Comparative Examples 6–10, the Wave Down phenomenon is improved with increases in the processing temperature, and the degree of improvement is remarkable in the case where a low-concentration hydrogen peroxide solution is used.

Surprisingly enough, it was found that Modulus Recovery Ratio also improves with increases in the processing temperature.

The degree of improvement of Modulus Recovery Ratio is remarkable in the case where a low-concentration hydrogen peroxide solution is used.

The degree of improvement of Modulus Recovery Ratio and Wave Down achieved by means of increasing the pH value is remarkable in the case where the hair is processed with the low-concentration hydrogen peroxide solution at a high processing temperature.

As is obviously learned form the foregoing, the hydrogen peroxide solution of the present invention comprising specific combinations of high pH value and low concentration exhibits excellent performance as the permanent waving lotion, and, furthermore, the characteristics of the present invention are exploited to higher degrees by conducting the permanent waving at such temperature levels as set forth as preferred embodiments in the the present invention.

According to the present invention using the aqueous solution of hydrogen peroxide whose pH value and concentration fall within certain ranges as the second lotion for permanent waving, decline in the modulus due to repeated permanent wavings is made by far lower than in the case where the conventional second lotion is used, and there is not felt any noticeable decrease of the stiffness of the hair due to permanent waving.

According to the conventional method of permanent waving, the efficiency of production of a lasting curl in the hair gradually drops and, in particular, it becomes difficult to impart a lasting curl in the end part of hair after each complete step of repeated permanent wavings. On the other hand, the method in the present invention enables efficient production of sufficient curl to ends of the hairs by permanent waving without damaging the hair.

A complete understanding of the invention may be obtained from the foregoing and following description thereof, taken in conjunction with the appended drawings, in which:

FIG. 1 is a graph illustrating the changes in Modulus Recovery Ratio of the hairs which have undergone five consecutive permanent wavings performed with the second lotion in the present invention and the conventional second lotion, respectively.

FIG. 2 is a graph illustrating the relationship between Modulus Recovery Ratio (G3/G0) of the hairs which have undergone three consecutive permanent wavings performed with the second lotion in the present invention and the conventional second lotion, respectively, and the pH value of aqueous solution of hydrogen peroxide.

FIG. 3 is a graph illustrating the relationship between Modulus Recovery Ratio (G3/G0) of the hairs which have undergone three consecutive permanent wavings performed with the second lotion, and the hydrogen peroxide concentration of aqueous solution of hydrogen peroxide.

FIG. 4 is a graph illustrating the relationship between Modulus Recovery Ratio (G3/G0) and Wave Down of the hair which has undergone three consecutive permanent wavings at 45° C. and the properties of the hydrogen peroxide solution.

FIG. 5 is a graph illustrating the relationship between Modulus Recovery Ratio (G3/G0) and Wave Down of the hair which has undergone three consecutive permanent wavings and the processing temperature of the second lotion.

I claim:

1. A permanent waving lotion consisting of a hydrogen peroxide solution having a pH value in excess of 4.5, but not exceeding 7.5, and a hydrogen peroxide concentration of 0.3 wt. % or lower.

2. A process for permanent waving of hair which comprises treating hair with the keratin reducible first lotion for permanent waving before and/or after mechanical shaping of hair, rinsing the hair, and oxidizing and fixing the shaped hair by treating the hair with the permanent waving lotion according to claim 1 as the second lotion.

3. A process for permanent waving of hair according to claim 2 wherein said treating of the hair with the second lotion is carried out at a temperature of 37° C.~47° C.

* * * * *